United States Patent [19]
Henalla

[11] Patent Number: 6,071,230
[45] Date of Patent: Jun. 6, 2000

[54] INSTRUMENT FOR GUIDING DELIVERY OF INJECTABLE MATERIALS IN TREATING URINARY INCONTINENCE

[75] Inventor: Samir Morris Henalla, Barnsley, United Kingdom

[73] Assignee: Uroplasty, Inc., Minneapolis, Minn.

[21] Appl. No.: 09/040,594

[22] Filed: Mar. 18, 1998

Related U.S. Application Data

[63] Continuation-in-part of application No. 08/752,038, Nov. 19, 1996, abandoned.

[51] Int. Cl.[7] .......................................... A61F 2/00
[52] U.S. Cl. ................................. 600/29; 604/19
[58] Field of Search ................... 600/29, 30, 33, 600/34, 35; 604/19, 51, 54, 55, 164, 93, 27, 117, 264, 280

[56] References Cited

U.S. PATENT DOCUMENTS 5,336,263  8/1994  Ersek et al. .
5,588,960  12/1996  Edwards et al. .

FOREIGN PATENT DOCUMENTS 2284158A  5/1995  United Kingdom .

*Primary Examiner*—Linda C. M. Dvorak
*Assistant Examiner*—R Kearney
*Attorney, Agent, or Firm*—Fulbright & Jaworski

[57] ABSTRACT

An introducer for facilitating the injection of a bulking agent into the urinary sphincter of a patient comprises a rigid tubular member having a closed distal end, an open proximal end and a lumen extending therebetween. The tubular member has an aperture in a side wall thereof leading to the lumen, the aperture being a known predetermined distance from the closed distal end. Integrally formed with the cylindrical tube is a flared wall structure in the shape of a hollow cone. Formed obliquely through the wall of the cone are a plurality of regularly radially spaced bores that exit the cylindrical tubular portion, a fixed, predetermined distance from the aforementioned aperture. By inserting the instrument into the urethra until urine flow is detected through the lumen of the guide and then withdrawing the instrument carefully until urine flow just ceases, when an injection needle of a predetermined length is inserted into the oblique bore, the sharpened tip of the injection needle will be appropriately positioned for depositing the bulking agent in a way to augment tissue surrounding the urinary sphincter.

13 Claims, 6 Drawing Sheets

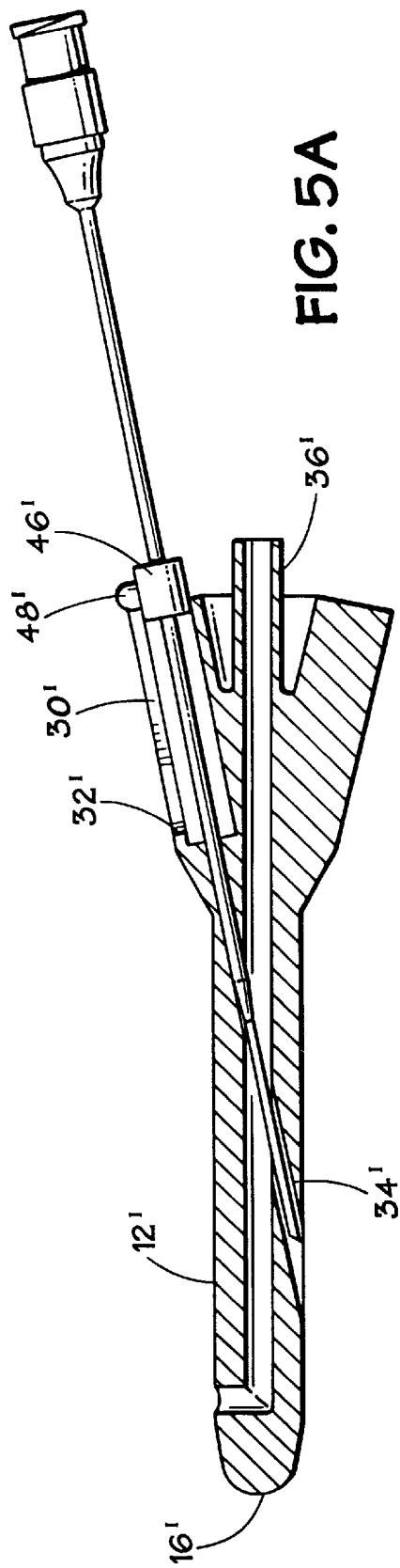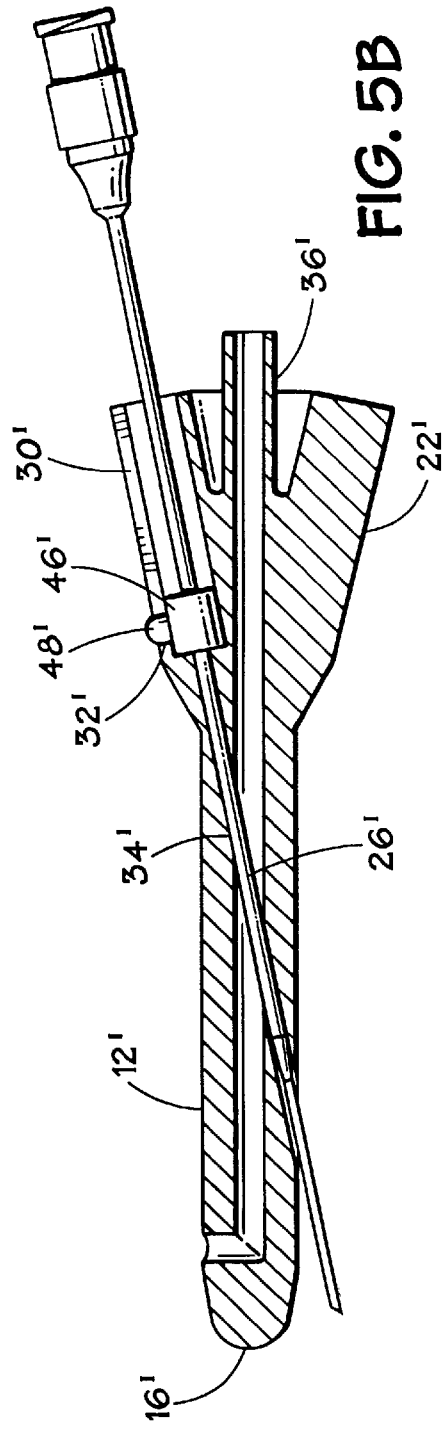

ately placed into the surrounding tissue at a location for augmenting the tissue proximate the urinary bladder neck or mid-uretherally, if appropriate.

INSTRUMENT FOR GUIDING DELIVERY OF INJECTABLE MATERIALS IN TREATING URINARY INCONTINENCE

CROSS-REFERENCE TO RELATED APPLICATION

This application is a continuation-in-part of application Ser. No. 08/752,038, filed Nov. 19, 1996, now abandoned.

BACKGROUND OF THE INVENTION

I. Field of the Invention:

This invention relates generally to surgical apparatus, and more particularly to an introducer to be used in accurately locating the injection site when treating female urinary stress incontinence by augmenting the tissue proximate the urinary sphincter with injectable materials.

II. Discussion of the Prior Art

In treating stress incontinence, especially in female patients, it has been found expedient to augment the tissue surrounding the urinary sphincter with injectable materials. In this regard, reference is made to the Ersek et al. U.S. Pat. No. 5,336,263, whose content is hereby incorporated by reference. As is explained therein, by injecting a mixture of solid micron-sized particles and a suitable fluid carrier intrauretherally so as to deposit the particles at the site of the urinary sphincter, the ability of the sphincter to cut-off urine flow during stress episodes, such as coughing, sneezing, laughing, etc., is enhanced.

In my published U.K. patent application 2,284,158A, I describe an instrument which I have termed an "injection catheter", that facilitates injection of substances for augmenting the tissue surrounding the bladder neck. That instrument comprises an outer tubular sheath having a proximal end, a closed distal end and a lumen extending therebetween. Formed a predetermined distance proximal to the closed distal end of the sheath is an aperture into which urine may flow when the catheter is inserted into the patient's urethra and advanced until the aperture passes beyond the bladder neck into the urinary bladder itself. A plurality of flexible injection needles are affixed to a common hub and the outer sheath includes a corresponding plurality of exit holes. When the needles are advanced through the lumen of the sheath to exit the openings in the sheath wall provided for them, an injectant can be delivered under pressure through the hub and simultaneously through the injection needles into the tissue to be augmented. The apertures on the sheath provide a reference for locating the distance that the sheath must be retracted so that the aperture through which the urine passes is at the bladder neck.

In using the device described in the aforereferenced U.K. patent application, the needles are made to penetrate through the urethral wall into the surrounding tissue to be augmented. I have found it preferable to intrauretherally inject tile augmenting substance and it is the principal object of the present invention to provide an instrument for accurately locating the entry point on the patient's body where the needle of an injection syringe penetrates so that a fluid suspension of injectable material may be accurately placed into the surrounding tissue at a location for augmenting the tissue proximate the urinary bladder neck or mid-uretherally, if appropriate.

SUMMARY OF THE INVENTION

The foregoing object and advantage of the invention is realized by providing an introducer that facilitates the accurate interuretheral injection of a bulking agent into the urinary sphincter of a patient that comprises a rigid tubular member of a predetermined length having a closed distal end, an open proximal end and a lumen extending therebetween. The tubular member includes an aperture in a side wall thereof that is in fluid communication with the instrument's lumen, the aperture being a predetermined distance proximal of the closed distal end of the rigid tubular member. A proximal end portion of the tubular member has a proximally and outwardly extending tapered wall portion that defines a concentric, conically-tapered cavity. A plurality of regularly spaced straight bores extend obliquely through the tapered wall portion of the instrument and exit the rigid tubular member at a predetermined angle. The straight bores are adapted to sequentially receive an injection needle of a predetermined size therethrough. In use, the tubular portion of the instrument is inserted into the patient's urethra and advanced until the aperture in the tubular member enters the urinary bladder, at which point an indication is given by virtue of a flow of urine through the tubular member and out its proximal end. The instrument is then backed off in the proximal direction until urine flow ceases. Markings on the tubular member allows one to determine the uretheral length, thus allowing for injection of the material in proximity to the bladder neck or mid-uretherally as may be desirable. At that point, the needle of the injection syringe can be inserted through the straight bores formed in the tapered wall portion of the instrument and the sharpened end will exit at an appropriate angle and for a distance that will place the sharpened tip of the needle at the desired location for augmenting the tissue of the urinary sphincter. Measured quantities of injectate may be delivered to different sites by moving the injection needle from one straight bore to another so as to effectively encircle the urinary sphincter.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

FIGS. 5A and 5B are similar to FIGS. 4A and 4B for an alternative embodiment of the invention.

DESCRIPTION OF THE PREFERRED EMBODIMENT

Figure 1:
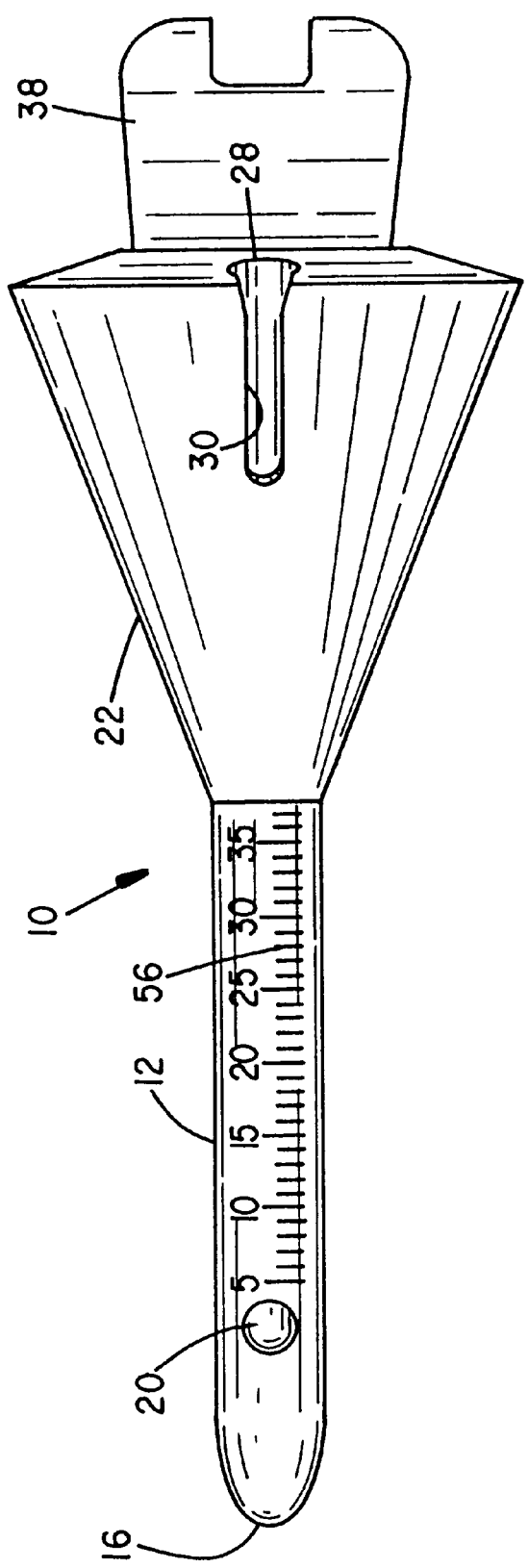
FIG. 1 is a top plan view of the instrument comprising a preferred embodiment of the present invention.

Referring first to FIG. 1, there is indicated generally by numeral 10 a preferred embodiment of an instrument for guiding the delivery of tissue augmenting substances to an annular zone surrounding a urinary sphincter in the treatment of incontinence. The instrument comprises a rigid generally tubular member 12 having an open proximal end 14 (FIG. 2), a closed distal end 16 and a lumen 18 extending therebetween. The tubular member 12 incudes an aperture 20 through the side wall thereof so as to be in fluid communication with the lumen 18. With no limitation intended, for use with an adult female patient, the distance between the distal end 16 of the tubular member 12 and the center of the aperture 20 may be about 0.453 in. and the outer diometer (O.D.) of the tubular segment 12 may be in the range of from 0.264 to 0.341 in. (20–26 Fr.). With such an O.D., when inserted in a patient in a manner to be described, the urethra is slightly distended.

Figure 2:
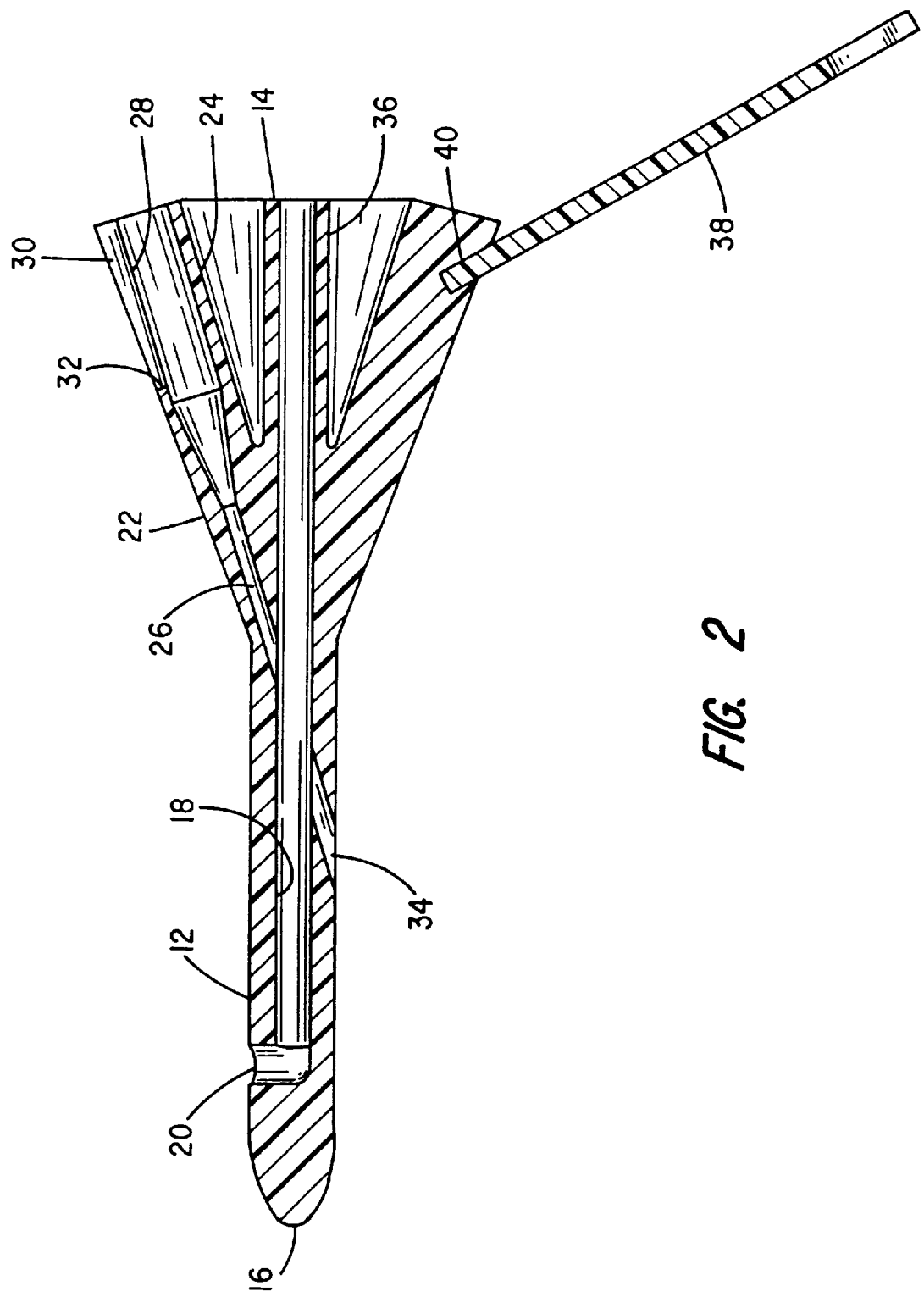
FIG. 2 is a longitudinal cross-sectional view thereof.

Flaring outward from the open proximal end portion of the cylindrical tubular segment 12 is a tapered conically-shaped wall 22 that defines a concentric, conically-tapered cavity 24 therein. With this embodiment, the angle of taper is about 17° with respect to a longitudinal axis of the tubular portion 12, but an angle anywhere in the range of from about 10° to 45° also proves workable. Extending obliquely through the wall 22 and exiting through the wall of the cylindrical segment 12 are a plurality (three) of regularly spaced bores as at 26 (FIG. 2). These straight bores 26 are 120° apart and are adapted to receive an injection needle, such as that shown in FIGS. 4A and 4B therethrough. To facilitate insertion of the injection needle into the bore, the proximal end portion 28 of each is funnel-shaped, thereby presenting an enlarged target. Slots, as at 30, extend through the wall 22 of the conical portion to define a stop 32. Again, in the case of an instrument intended for use in treating an adult female patient, the exit holes 34 of the obliquely extending bores 26 may be in a range of from about 0.65 to 1.3 in. from the center of the aperture 20.

The extension stem 36 of the tube 12 contained within the conical cavity 24 is intended to mate with a fitting on the end of a urine collection tube (not shown).

Completing the assembly is a handle 38 which may be smooth for ease of cleaning where the instrument is to be reused, but which may also have a knurled exterior (FIG. 3) for ease of grasping and holding when wearing surgical gloves. The handle 38 may, for example, be about 1–½ in. in length and extends at an angle of about 60° to the longitudinal axis of the rigid tubular member 12 to fit into a slot 40 formed in the wall 22 where it is bonded or welded in place. The handle 38 and the needle guide member may be molded or machined from a suitable medical grade plastic, such as polycarbonate, polyethylene or Delrin, etc., or any biocompatible and non-corrosive metal or alloy such as stainless steel 316L. Depending on production economies, the device may be comprised of several parts or may comprise a unitary (one-piece) structure.

Figure 3:
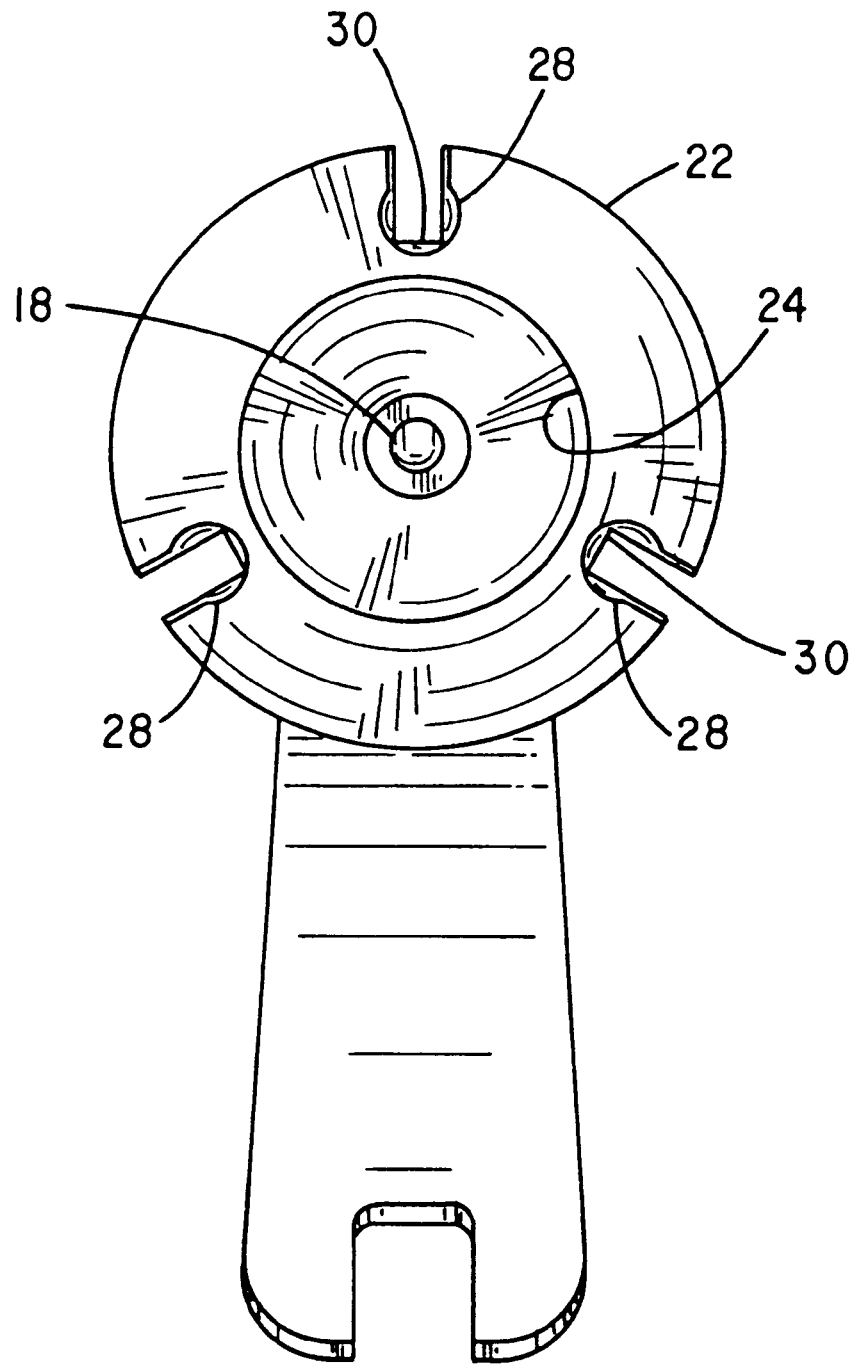
FIG. 3 is a rear view thereof.
Figure 4A:
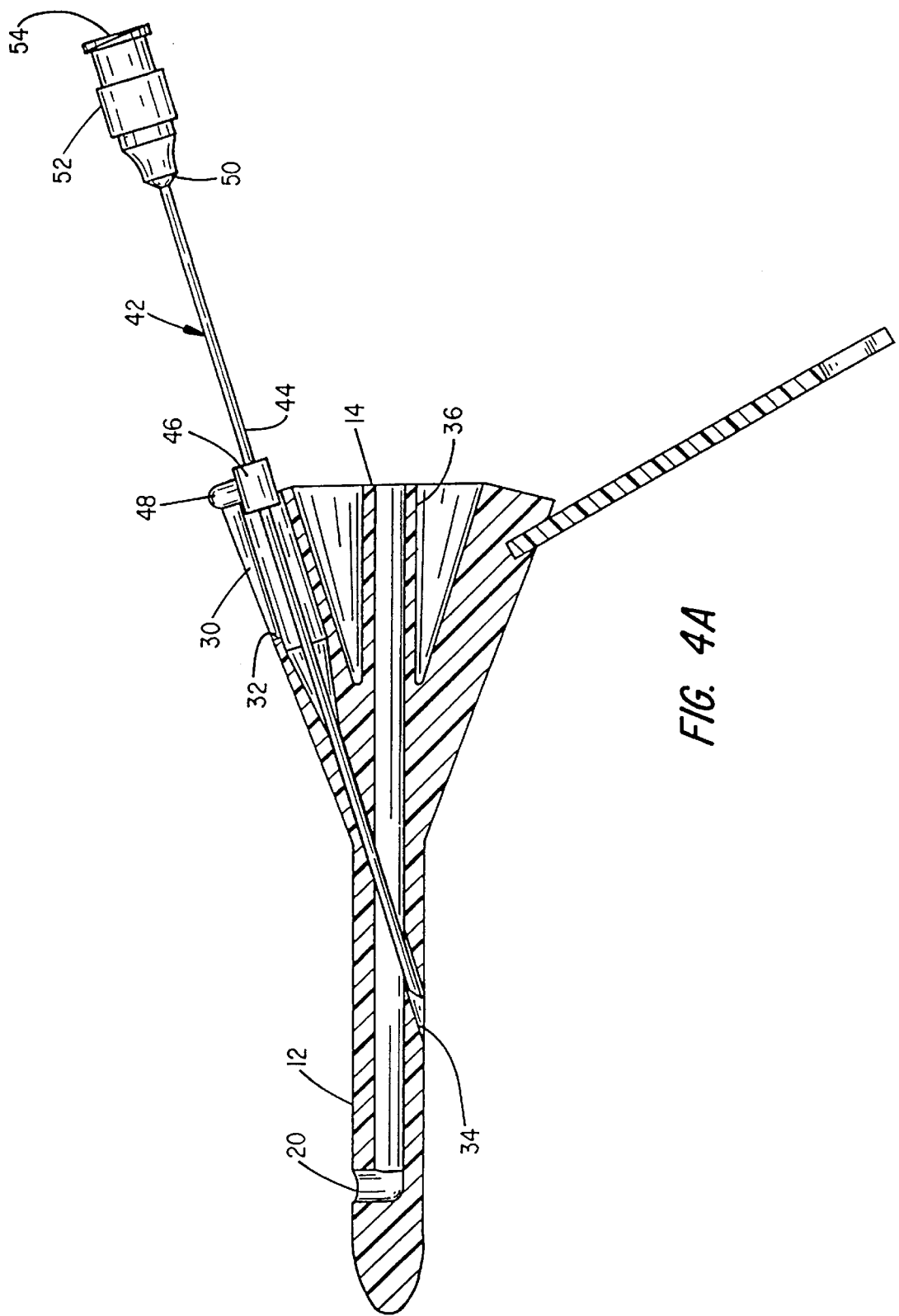
FIGS. 4A and 4B illustrate an injection needle being used with the instrument of FIG. 1.
Figure 4B:
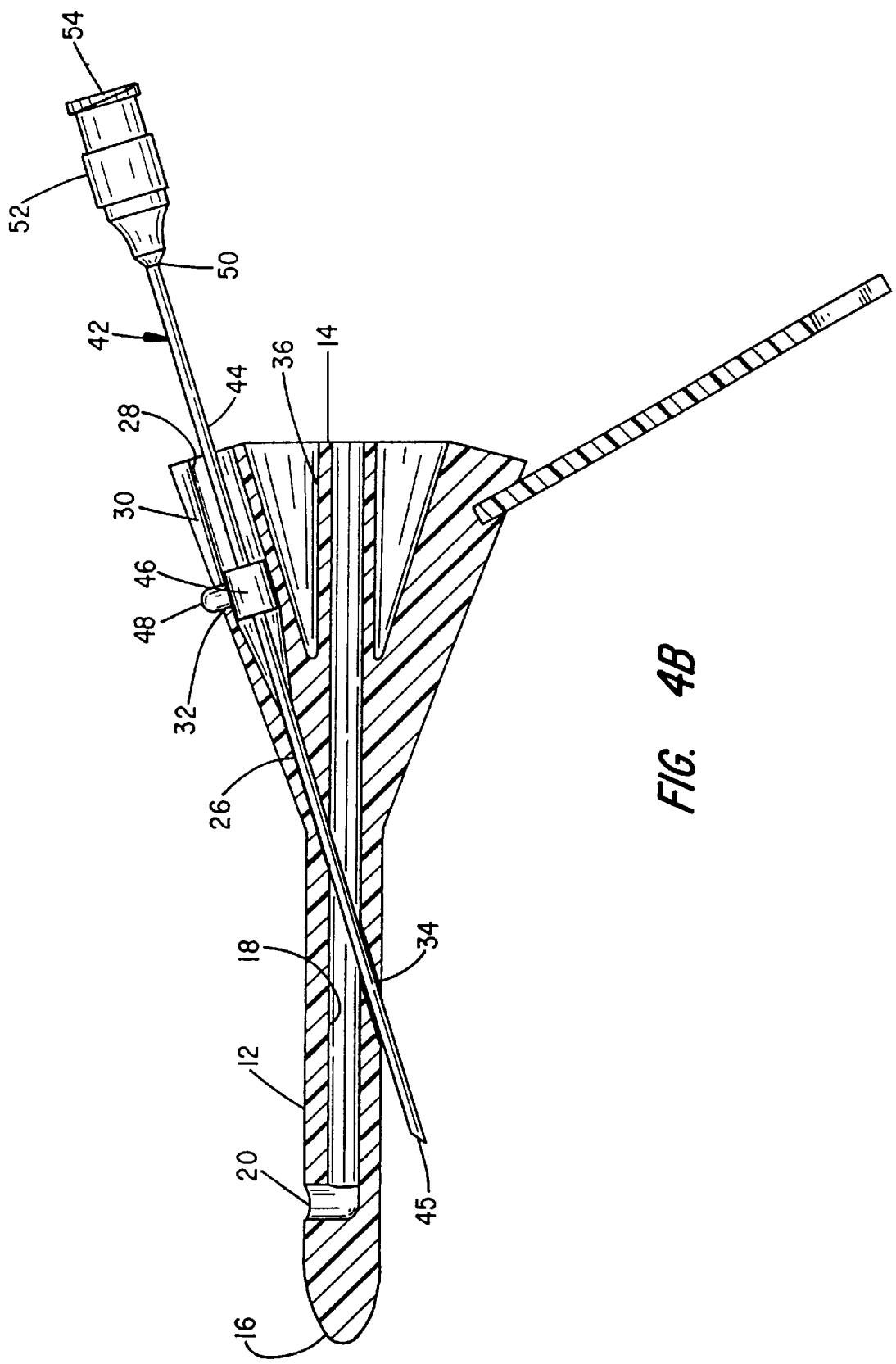

Referring next to FIGS. 4A and 4B, identified by numeral 42 is an injection needle designed for use in injecting the injectable material using the guide of FIGS. 1–3 to accurately deposit the injectable material in a zone which will augment the tissue about the urinary sphincter and thereby enable the sphincter to better control urination. It comprises a hollow needle member 44 formed of stainless steel and having a sharpened distal end 45 to facilitate its penetration through tissue. The needle may have an outside diameter in the range of 0.0355 in. to 0.0505 in. and a corresponding inside diameter of 0.0255 in. to 0.0430 in.

Affixed to the needle shaft a predetermined distance from the sharpened distal end is a hub 46 that is bonded in place by soldering or other suitable means. Located on the rounded surface of the hub 46 is an indicator 48 that is aligned with the beveled point 45 so that the surgeon may be aware at all times of the angular positioning of the beveled point.

Affixed to the proximal end 50 of the needle 44 is a metal hub 52 having a Luer lock fitting 54 on its proximal end for mating with an injection syringe (not shown). The length of the needle between the distal edge of the hub 46 and the sharpened end 45 of the needle may be about 2.143 in., this length being appropriate for use with the guide instrument of FIGS. 4A and 4B. With the bore 34 inclined at an angle of 17° to the longitudinal axis of the lumen 18, a needle of this length will have its sharpened tip about 4 mm from the side wall of the tubular member 12 when the indicator 48 abuts the stop 32.

OPERATION

In use, a suitable lubricant may be applied to the exterior surface of the cylindrical tubular portion 12 of the instrument and then the bullet-shaped distal end 16 will be inserted into the exterior opening of the urethra. The surgeon will advance the instrument through the urethra until a trickle of urine is seen to exit the proximal end of the stem portion 36 of device 10, at which point it is known that the aperture 20 is located in the urinary bladder, providing a point of reference. The surgeon will then draw back on the handle 38 slowly until the trickle of urine just ceases, at which point it is known that the aperture 20 resides in the bladder neck. The graduated marking 56 (FIG. 1) on the cylindrical tubular portion allows for determining the length of the urethra. Using one hand to hold the handle 38 in place at this location, the surgeon will use his other hand to grasp an injection syringe containing the particulate material in a lubricious fluid carrier and having a needle 42 on it of the type illustrated in FIGS. 4A and 4B. The sharpened point 45 of the needle will be inserted into the funnel-shaped opening 28 of one of the regularly spaced, obliquely directed straight bores 26 and will advance the needle through that selected bore. The indicator 48 will be guided into the slot 30 on the cone-shaped wall 22 until it abuts the stop 32 defined by the distal end of this slot. Because of the dimensions and geometry employed in the guide device 10, the pointed end of the injection needle 45 will be a zone surrounding the patient's urinary sphincter. The surgeon will then depress the syringe plunger and eject a quantity of bulking material. The surgeon will then withdraw the needle from the straight bore that had been used for the first injection and will move it to a different one of the regularly-spaced bores 26 where the injection step will again be repeated. The process may again be repeated until a predetermined measured quantity of injectate has been uniformly distributed in the zone surrounding the urinary sphincter.

As is apparent from FIG. 4B of the drawings, with the previously described embodiment, the bulking agent will be injected into tissue surrounding the urethra but at a location where the guide 10 has its tubular member 12 residing in the urethra at the site where the micron-sized particles are deposited. Because of the presence of the tubular member 12 within the urethra at the site where the injection is made, tissue is not allowed to expand into the urethra because of the pressure exerted by the tubular member 12 on the tissue that is to be bulked up by the injectate. The alternative embodiment shown in FIGS. 5A and 5B can be used to provide bulking of tissue surrounding the urethra at a location at or forward of the distal end of the probe, allowing the injected tissue to expand into the urethral space and closing off the otherwise open urethra.

The embodiment of FIGS. 5A and 5B is substantially like the earlier described embodiment except that the angle of the tapered, conically-shaped wall 22' is somewhat shallower, for example, about 12½° with respect to the longitudinal axis of the instrument rather than about 17° as in the earlier described embodiment of FIGS. 1–4. In that the taper of the conically-shaped wall is more shallow, so too is the angle of the bores 34' that extend through the conical wall and through the tubular member 12'. By having a shallower angle, the exit point of the bore 34' from the tubular member 12' is located closer to the distal end 16' of the instrument allowing a somewhat longer needle 26' to be employed such that the sharpened distal tip 45' thereof will reach very close to the distal end 16' of the instrument and with only a small distance or gap between the tip 45' of the fully inserted needle and the wall of the tubular member which defines the depth of penetration of the needles into the tissue surrounding the uretheral.

The mode of operation or method of use of the embodiment of FIGS. 5 and 5A is substantially identical to the mode of use of the present invention except that by providing a shallower angle of the bore 34' relative to the longitudinal axis of the instrument, the injected material will be located very close to the distal end 16' of the instrument allowing the bulked tissue to better close off the urethral channel, thus promoting continence.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An introducer for facilitating the accurate injection of a bulking agent into the urinary sphincter of a patient comprising:
   (a) a rigid tubular member of a predetermined length having a closed distal end, an open proximal end and a lumen extending therebetween, the tubular member including an aperture in a side wall thereof in fluid communication with the lumen, the aperture being a predetermined distance proximal of the closed distal end, the open proximal end having a tapered wall portion extending proximally and outwardly at a predetermined angle to define a concentric, conically-tapered cavity; and
   (b) a plurality of regularly spaced straight bores extending obliquely through the tapered wall portion and exiting the rigid tubular member at said predetermined angle, said straight bores adapted to receive an injection needle of a predetermined diameter and length therethrough.

2. The introducer as in claim 1 and further including a handle member affixed to the tapered wall portion of the rigid tubular member.

3. The introducer as in claim 1 wherein the closed, distal end is smoothly rounded.

4. The introducer as in claim 1 wherein the predetermined length of the tubular member distal of the tapered wall portion is sufficient to locate the aperture in the side wall within the urinary bladder of a patient when the tapered wall portion is exterior to the patient's urethral meatus.

5. The introducer as in claim 4 wherein the predetermined angle is in a range from about 10° to 45° to a longitudinal axis of the lumen.

6. The introducer as in claim 4 wherein the predetermined angle is about 17° to a longitudinal axis of the lumen.

7. The introducer as in claim 4 wherein the predetermined angle is about 12.5° to a longitudinal axis of the lumen.

8. The introducer as in claim 6 wherein the plurality of straight bores exit the rigid tubular member at a distance in a range from 0.65 to 1.3 in. proximal of the aperture in the side wall of the tubular member.

9. The introducer of claim 8 wherein the plurality of straight bores exit the rigid tubular member at a distance of about 0.80 in. proximal of the distal end of the tubular member.

10. The introducer as in claim 1 wherein the plurality of spaced bores include a tapered entry.

11. The introducer as in claim 1 wherein the outside diameter of the injection needle receivable in the straight bores is in the range of from about 0.0355 to 0.05050 in.

12. The introducer as in claim 1 wherein graduated markings are provided on the rigid tubular member to allow for determining the uretheral length, providing for accurate placement of the bulking agent.

13. The introducer as in claim 1 wherein one outside diameter of the tubular member distal of the tapered wall portion is sufficient in circumference to slightly stretch the urethra.

* * * * *